(12) United States Patent
Liu et al.

(10) Patent No.: US 10,045,847 B2
(45) Date of Patent: Aug. 14, 2018

(54) ELECTRIC HANDLE FOR IMPLANT DELIVERY AND DELIVERY SYSTEM

(71) Applicant: SHANGHAI MICROPORT MEDICAL (GROUP) CO., LTD., Shanghai (CN)

(72) Inventors: Xiang Liu, Shanghai (CN); Zhixiu He, Shanghai (CN); Yu Li, Shanghai (CN); Baozhu Gui, Shanghai (CN); Mingming Wu, Shanghai (CN); Haishan Wang, Shanghai (CN); Qiyi Luo, Shanghai (CN)

(73) Assignee: Shanghai Microport Cardioflow Medtech Co., Ltd., Shanghai (CN)

(*) Notice: Subject to any disclaimer, the term of this patent is extended or adjusted under 35 U.S.C. 154(b) by 350 days.

(21) Appl. No.: 14/894,270

(22) PCT Filed: May 26, 2014

(86) PCT No.: PCT/CN2014/078398
§ 371 (c)(1),
(2) Date: Nov. 25, 2015

(87) PCT Pub. No.: WO2014/190880
PCT Pub. Date: Dec. 4, 2014

(65) Prior Publication Data
US 2016/0100943 A1   Apr. 14, 2016

(30) Foreign Application Priority Data
May 27, 2013   (CN) .......................... 2013 1 0202016

(51) Int. Cl.
*A61F 2/24*   (2006.01)
*A61F 2/966*   (2013.01)
*A61F 2/95*   (2013.01)

(52) U.S. Cl.
CPC ............ *A61F 2/2436* (2013.01); *A61F 2/966* (2013.01); *A61F 2002/9517* (2013.01)

(58) Field of Classification Search
CPC .... A61F 2/2436; A61F 2/2427; A61F 2/2439; A61F 2/95; A61F 2002/9517;
(Continued)

(56) References Cited
U.S. PATENT DOCUMENTS 5,389,073 A    2/1995   Imran
6,402,760 B1 *  6/2002   Fedida ...................... A61F 2/95
                                                604/528
(Continued)

FOREIGN PATENT DOCUMENTS

CN    1961847     5/2007
CN    101553190   10/2009
(Continued)

*Primary Examiner* — Jonathan Miles
(74) *Attorney, Agent, or Firm* — Muncy, Geissler, Olds & Lowe, P.C.

(57) ABSTRACT

An electric handle for delivering an implant is disclosed. The electric handle (1) includes an electric control unit (10), a power-driven transmission mechanism (20), a handle housing (30), an outer tube anchor (40) and an inner tube anchor (50), wherein: the electric control unit (10) is operatively coupled to the power-driven transmission mechanism (20) to actuate the power-driven transmission mechanism (20); the power-driven transmission mechanism (20) is supported within the handle housing (30) and moveable together with the outer tube anchor (40); the inner tube anchor (50) is disposed within the handle housing (30) and is configured to hold an inner tube (3) of a delivery system; and the outer tube anchor (40) is configured to hold an outer tube (2) of the delivery system and is fixed to an end of the outer tube (2). A delivery system used especially for delivery of prosthetic valves is also disclosed, including an outer tube (Continued)

(2), an inner tube (3), an expandable implant (4) and the electric handle (1).

14 Claims, 3 Drawing Sheets

(58) Field of Classification Search
CPC .. A61F 2/954; A61F 2/958; A61F 2002/9583; A61F 2/962; A61F 2/966; A61F 2002/011
See application file for complete search history.

(56) References Cited

U.S. PATENT DOCUMENTS

| | | |
|---|---|---|
| 6,764,494 B2 | 7/2004 | Menz et al. |
| 2011/0251683 A1 | 10/2011 | Tabor |
| 2013/0123757 A1 | 5/2013 | Crisostomo et al. |

FOREIGN PATENT DOCUMENTS

| | | |
|---|---|---|
| CN | 101612436 | 12/2009 |
| CN | 101961269 | 2/2011 |
| CN | 103110441 | 5/2013 |
| CN | 102573703 B | 12/2014 |
| WO | WO 2012116368 | 8/2012 |

* cited by examiner

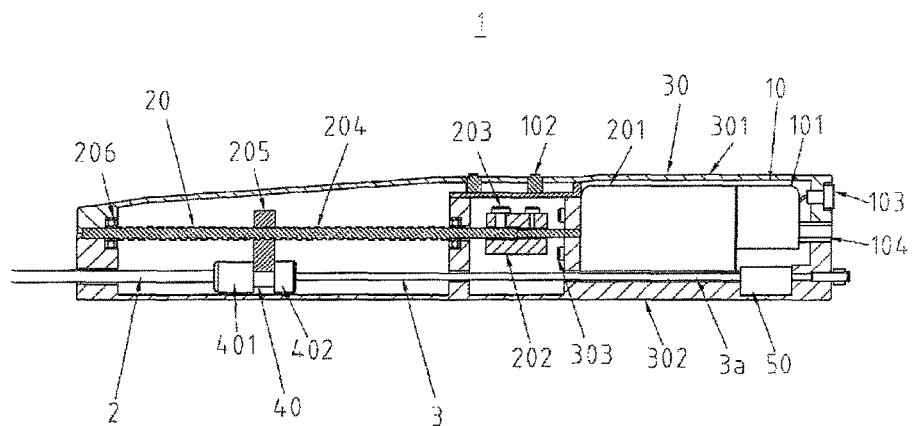
FIG. 1
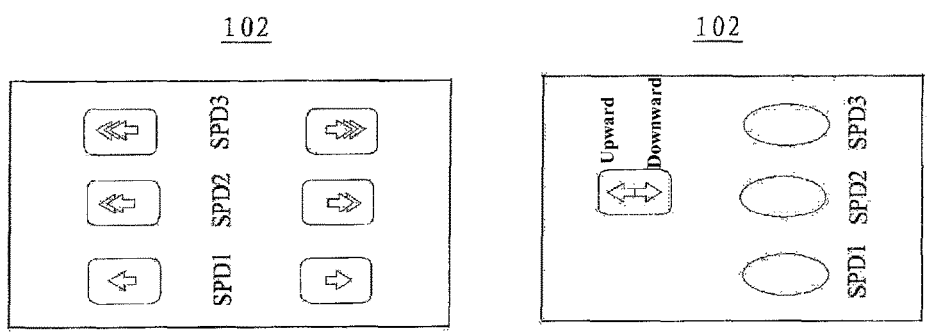
FIG. 2a
FIG. 2b

ELECTRIC HANDLE FOR IMPLANT DELIVERY AND DELIVERY SYSTEM

TECHNICAL FIELD

The present invention relates generally to medical instruments and, in particular, to delivery devices for delivering and placing an implant (e.g., a prosthetic valve or a blood vessel stent). Specifically, in a first aspect, the invention is directed to an electric handle for delivering an implant. In a second aspect, the invention is directed to an implant delivery system incorporating an electric handle.

BACKGROUND

Heart valve diseases are some of the most common cardiac diseases in China, and most of them are valve damage caused by rheumatic fever. In recent years, the aging population has led to an increasing incidence of valve degeneration (including calcification, mucoid degeneration, etc.) and valve damage caused by metabolic disorders in China.

Conventionally, heart valve surgery is an open-heart procedure conducted under general anesthesia, during which, following an incision made along the patient's sternum (sternotomy), the heart is stopped and blood flow is guided through a "heart-lung" bypass machine (extracorporeal circulation machine). Therefore, traditional heart valve replacement surgery is a highly traumatic operation with obvious accompanied risks and may bring to the patient transient disturbances caused by emboli and other issues associated with the use of the extracorporeal circulation machine, such that a complete recovery typically requires a couple of months. In addition, for the elders and some special population groups, the trauma of the surgery is unbearable and the recovery needs more time and is sometime even impossible.

Minimally invasive interventional surgery offers a variety of advantages, including needlessness of sternotomy, minimal trauma and quick recovery for the patients. In the recent ten years, interventional therapies have shown a tendency to be able to cope with not only all diseases curable by medical and surgical treatments but also some diseases that the surgical treatments could not handle. After entering the twenty-first century, researches on interventional therapies for heart valve diseases have been experiencing a notable acceleration. Percutaneous valve replacement technologies have evolved from experimental researches to small-scale clinical trials and the interventional therapies for heart valve diseases are likely to have breakthroughs in technical "bottlenecks" to achieve extensive clinical applications. This makes the technologies again a focus of research efforts in the field of interventional cardiology.

Currently, many manual delivery systems for a prosthetic valve have been developed. Examples of such delivery systems include those disclosed in Chinese Patent Application No. 201010150770.6 assigned to Hangzhou Venus Medical Instrument Co., Ltd., Chinese Patent Application No. CN200510110144.3 assigned to Wen Ning, Chinese Patent Application No. CN201080046790.7 assigned to Medtronic, Inc. (the U.S.) and Chinese Patent Application No. CN200780008324.8 assigned to Edwards Lifesciences Corp. (the U.S.). Mostly, these systems include an inner tube, an outer tube, a prosthetic valve and a push-pull mechanism. The inner tube includes a guide cone, a connector for the prosthetic valve, and the prosthetic valve is loaded on an intermediate section between the guide cone and the connector for the prosthetic valve of the inner tube and securely attached to the connector. The outer tube shields over the inner tube in order to cover the prosthetic valve and is movable along the outer surface of the inner tube. The push-pull mechanism is in operative connection with the guide cone of the inner tube as well as with the outer tube so as to deploy the prosthetic valve.

However, the manual delivery systems currently used for interventional procedures involves sophisticated operations, imposes demanding requirements on the operating physician and raises a considerable amount of risk in terms of faulty operations. Additionally, the required operations are laborious and prone to cause hand fatigue of the physician, which is one of the reasons that cause inaccuracy of the operation or misoperations and hence deterioration in surgical performance.

U.S. Patent Pub. No. US20110251683A1 discloses an improved delivery system which can be operated in two different modes, i.e., rotation and advancement/retraction, enabling different delivery speeds. This delivery system includes a mechanical actuator mechanism which in practical use can be manually rotated or advanced/retracted to perform corresponding control functionality. However, this mechanical delivery system has the following drawbacks:

1) It involves sophisticated operations, imposes demanding requirements on the operating physician and raises a considerable amount of risk in terms of faulty operations;

2) The required operations consist of manual rotation and push/pull motions, which are laborious and require the use of both hands. This tends to cause hand fatigue of the physician and thus affects accuracy of the operation and performance of the surgical procedure.

3) It suffers from imprecise catheter motions. Advancement or retraction of the outer tube in the delivery system is enabled by the physician manually pushing, pulling or rotating a proximal handle, which lacks accurate and reliable control of the outer tube's velocity and motion.

SUMMARY OF THE INVENTION

It is therefore an objective of the present invention to provide a control handle and a delivery system for controlled deployment of a prosthetic valve being delivered, which allow the prosthetic valve to be positioned to a target site at a controlled speed in a reliable and accurate manner and can be operated by a physician with a single hand.

To this end, the present invention provides an electric handle for a delivery system for delivering an implant, particularly a prosthetic valve. By means of electric control, the handle enables, for example, loading, positioning, deploying and retrieving of the prosthetic valve as well as outer tube recovery. In accordance with the present invention, the electric handle includes an electric control unit, a power-driven transmission mechanism, a handle housing, an outer tube anchor and an inner tube anchor, wherein the electric control unit is operatively coupled to the power-driven transmission mechanism in order to actuate the power-driven transmission mechanism; the power-driven transmission mechanism is supported within the handle housing and moveable together with the outer tube anchor; the inner tube anchor is disposed within the handle housing to hold an inner tube of a delivery system; and the outer tube anchor is disposed within the handle housing to hold an outer tube of the delivery system.

According to embodiments of the present invention, the electric control unit includes a controller, control buttons, a power switch, a power supply socket and a power supply connector. The controller receives an instruction from the control buttons and converts the instruction into a signal recognizable by the power-driven transmission mechanism so as to actuate the power-driven transmission mechanism. The power switch is connected to the controller or the control buttons via a cable so as to activate or deactivate the controller. The power supply socket is coupled to the power supply connector, and the power supply connector is connected to a power supply so as to supply power to the electric control unit and the power-driven transmission mechanism. The controller may either be integrated with the control buttons, or be integrated with the motor of the power-driven transmission mechanism then connected to the control buttons. The control buttons are configured to provide the instruction indicative of a direction and a speed. In one embodiment of the present invention, the number of the control buttons is six, and the control buttons are divided into two groups corresponding respectively to advancement and retraction operations. In each of the groups, the three buttons correspond respectively to three speed gears for the respective direction. In another embodiment of the present invention, the control buttons include one direction button, i.e., an "Upward/Downward" button corresponding to the advancement/retraction operations, and three speed buttons correspond respectively to the three speed gears. In accordance with embodiments disclosed herein, the three speed gears are a first gear, a second gear and a multi-speed gear. It is a matter of course that more or less speed gears may also be arranged according to practical needs.

Preferably, the power supply is integrated in the electric handle. Of course, the power supply may also be implemented as an external power source. In this case, the power supply connector may include a power supply plug, an adapter and a connecting plug, which are connected by a cable in this order. The connecting plug is configured to be coupled to the power supply socket.

According to embodiments of the present invention, the power-driven transmission mechanism includes a motor, a shaft coupler, a threaded rod, a driving nut and a bearing, wherein the motor is connected to the power supply socket and receives the signal from the controller; an output of the motor is coupled to the threaded rod via the shaft coupler; the threaded rod is supported within the handle housing by the bearing; and the threaded rod has an outer thread that engages an inner thread of the driving nut.

Preferably, the power-driven transmission mechanism further includes a fastening screw, through which the threaded rod is fastened to the shaft coupler.

According to embodiments of the present invention, the outer tube anchor includes an anchor nut and an outer tube anchor block, wherein the anchor nut is fixed to one end of the outer tube; the outer tube anchor block has an outer thread that engages an inner thread of the anchor nut; and the outer tube anchor block is coupled to a lateral end of the driving nut so as to move in synchronization with the driving nut.

Preferably, the inner tube anchor is fastened to the inner tube by a screw fit and is fixed within the handle housing.

According to embodiments of the present invention, the handle housing is comprised of an upper section and a lower section, wherein the motor is fastened on the lower section using a fastening screw; the inner tube anchor is fixed to the lower section; one end of the inner tube of the delivery system distal to the guide cone is coupled to the inner tube anchor with an adhesive or fastener, so that the inner tube is also secured to the lower section due to the inner tube anchor; and the control buttons, the power switch and the power supply socket are all attached to the upper section using an adhesive or fastener.

Enablement of advancement, retraction and selection of different speeds through manipulating the control buttons on the electric handle significantly increases convenience in the physician's operations, results in increased operating convenience and accuracy, and eliminates the need of the physician to exert push or rotating forces during the release process, thereby improving operating stability.

Therefore, the electric handle consistent with the present invention is capable of operating with high motion accuracy, high motion stability and reliable speed control, ensuring the prosthetic valve to be positioned to a target location in an accurate and reliable manner, and allowing the physician to operate it with a single hand in a simple and convenient way.

The present invention further provides a delivery system able to be used to deliver an implant. In accordance with the present invention, the implant delivery system includes the above-defined electric handle, an outer tube, an inner tube and the implant. The inner tube includes a guide cone and a connector for the implant. The implant is loaded on the section of the inner tube where it is located between the guide cone and the connector for the implant and attached to the connector for the implant. The outer tube shields over the inner tube in order to cover the implant and being movable along the outer surface of the inner tube. The outer tube and the inner tube each has a portion proximal to the connector for the implant that is at least partially assembled into the electric handle. The outer tube anchor so holds the outer tube that the outer tube moves together with the outer tube anchor. An end of the inner tube opposite to the guide cone is fixed within the handle housing by the inner tube anchor.

According to embodiments of the present invention, the implant is a prosthetic valve such as, for example, a heart valve. Of course, the inventive delivery system may also be used to deliver a blood vessel stent or other implants.

The delivery system according to the present invention allows direction selection and controlled speeds, which enable loading, positioning, deploying and retrieving of the prosthetic valve as well as recovery of the outer tube. All of these operations can be accomplished in a convenient and simple way with consistent quality. Thus, the delivery system achieves high operating accuracy and robustness and can be operated by the physician with a single hand without fatigue.

The present invention offers the following advantages:

1) It simplifies the operation through a button-activated power motor instead of the manual operations, and can be performed by a single physician.

2) The button-activated power motor avoids the use of large physical forces in the manual operation and thus avoid operation fatigue during surgery and improve surgical performance.

3) The physician is allowed to select a proper direction and speed of the delivery system for a specific need in the surgery, which can achieve reliable and accurate positioning and deploying of the prosthetic valve.

BRIEF DESCRIPTION OF THE DRAWINGS

The features and advantages of the present invention will become readily apparent from the following detailed description of a few embodiments thereof, which is to be read in connection with the accompanying drawings. It is apparent that the embodiments set forth below are only a part, but not all, of the possible embodiments of the present invention. In light of the teachings of the embodiments disclosed herein, those skilled in the art can make all other possible embodiments without exerting creative efforts, and all these embodiments are also embraced in the scope of this invention. In the drawings:

FIG. 1 is a schematic cross-sectional view of a electric handle constructed in accordance with an embodiment of the present invention;

FIGS. 2a to 2b diagrammatically show two control button arrangements for a control unit of a delivery system according to the present invention;

FIGS. 6a to 6c schematically illustrate a process of deploying a prosthetic valve, in which FIG. 6a shows the prosthetic valve in a pre-deploy state; FIG. 6b shows the prosthetic valve in a partially deployed state; and FIG. 6c shows the prosthetic valve in a deployed state.

LIST OF REFERENCE NUMERALS

Figure 3:
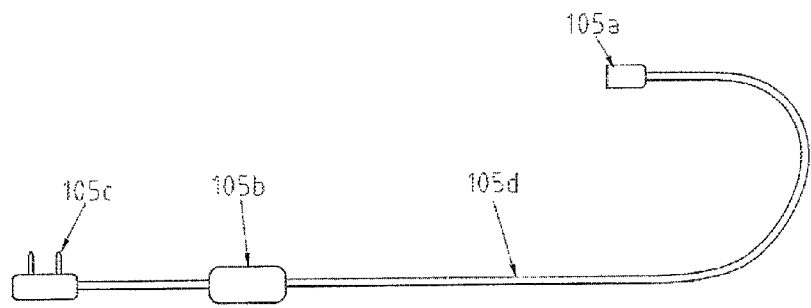
FIG. 3 is a schematic illustration of a power supply connector in a delivery system according to the present invention.

1 Electric handle; 2 Outer Tube; 3 Inner Tube; 3a Inner tube Section of the Inner Tube; 3b Connector for the Implant; 3c Stent-supporting Section of the Inner Tube; 3d Guide Cone; 4 Prosthetic Valve; 10 Electric Control Unit; 20 Power-driven Transmission Mechanism; 30 Handle Housing; 40 Outer tube Anchor; 50 Inner tube Anchor; 101 Controller; 102 Control Buttons; 103 Power Switch; 104 Power Supply Socket; 105 Power Supply Connector; 105a Connecting Plug; 105b Adapter; 105c Power Supply Plug; 105d Cable; 201 Motor; 202 Shaft Coupler; 203 Fastening Screw; 204 Threaded Rod; 205 Driving Nut; 206 Bearing; 301 Upper Section; 302 Lower Section; 303 Fastening Screw; 401 Outer tube Anchor Nut; 402 Outer tube Anchor Block

DETAILED DESCRIPTION

A few preferred embodiments of the present invention are described below with reference to the drawings which illustrate several examples of electric handles and delivery systems consistent with the present invention. Although the following description is made in the context of the delivery of a prosthetic valve, it is to be understood that the present invention is not limited to this regard as it is also useful in the delivery of other implants such as a blood vessel stent.

FIG. 1 illustrates an electric handle 1 of the present invention, including an electric control unit 10, a power-driven transmission mechanism 20, a handle housing 30, an outer tube anchor 40 and an inner tube anchor 50.

As shown in FIG. 1, the control unit 10 is comprised of a controller 101, control buttons 102, a switch 103, a power supply socket 104 and a power supply connector 105.

The controller 101 serves as a signal conversion unit for receiving an instruction from the control buttons 102 and converting the instruction into a signal that can be recognized by the power-driven transmission mechanism 20. This enables triggering of an actuation event. The instruction from the control buttons 102 is indicative of a direction and speed. FIG. 2a shows an arrangement of the control buttons, totaling six buttons, divided into two groups each having three buttons corresponding to three respective speed gears "SPD1" to "SPD3". Buttons marked with arrows pointing to opposite directions correspond respectively to "advancement" and "retraction". FIG. 2b shows another arrangement of the control buttons consisting of one direction control button, i.e., the "Upward/Downward" button corresponding to the "advancement" and "retraction" and three speed control buttons "SPD1" to "SPD3". The three speed gears may be set as a first gear, a second gear and a multi-speed gear depending on practical needs.

The switch 103 is connected to the controller 101 via a cable and is either in an "ON" or "OFF" state which corresponds to either activating or deactivating the controller 101. This can prevent a misoperation due to inadvertent touch of one or more of the control buttons 102 during the delivery of the prosthetic valve 4.

The electric control unit 10 can be powered by an external source (e.g., a surgery power supply) via the power supply socket 104 and power supply connector 105. It is a matter of course that it may also be powered by a power supply (e.g., a battery) embedded in the electric handle in order to facilitate portability of the electric handle. In case of an external power supply, the power supply connector 105 may be comprised of a connecting plug 105a, an adapter 105b, a power supply plug 105c and a cable 105d, as shown in FIG. 3. The connecting plug 105a is connected to the power supply socket 104, and the adapter 105b is provided to convert a surgery voltage to a voltage desired by the electric control unit 10.

The power-driven transmission mechanism 20 is comprised of a motor 201, a shaft coupler 202, a fastening screw 203, a threaded rod 204, a driving nut 205 and a bearing 206.

The motor 201 is driven by the electric control unit 10 to operate in a certain pattern. This process includes: the operator manipulating the control buttons 102 to select a desired direction and speed; the control buttons providing an instruction that is transmitted to the controller 101 via a cable; the controller 101 performing an internal operation, producing an instruction signal that is recognizable by the motor 201 and transmitting to the motor 201; the motor 201 rotating according to the signal. Additionally, based on the signal from the electric control unit 10 via a cable, the motor 201 can start rapidly, stop or continue rotating. An output of the motor is coupled to the threaded rod 204 by the shaft coupler 202 and fastening screw 203. The threaded rod 204 is supported on the handle housing by the bearing 206. An outer thread of the threaded rod 204 can engage an inner thread of the driving nut 205, thereby enabling conversion of rotation of the motor 201 into axial translation of the driving nut 205. The motor 201 may also be powered by an external or embedded power supply via the power supply socket 104 as well as the power supply connector 105.

The handle housing 30 is comprised of an upper section 301 and a lower section 302. The motor 201 is fastened on the lower section 302 by a fastening screw 303, and the inner tube 3 is fixed on the lower section 302 by the inner tube anchor 50. An adhesive or fastener is used to secure the control buttons 102 and power switch 103 on the upper section, and the power supply socket 104 on the lower section. Of course, in order to facilitate the overall assembly, the handle housing 30 may also be provided as a structure comprised of a left section and a right section, with the internal assembly attached to the respective sections or fixable when the two sections are assembled together.

Figure 4:
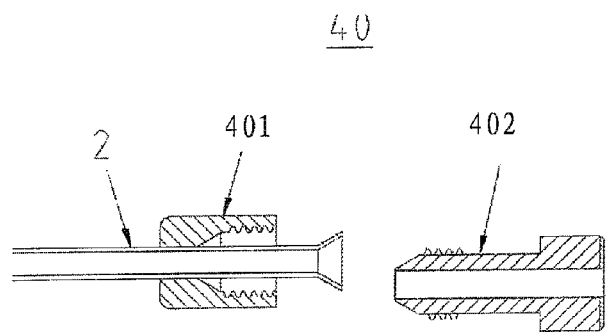
FIG. 4 is a schematic illustration of an outer tube anchor in a delivery system according to the present invention.

One end of the outer tube 2 is fixed to the outer tube anchor 40. As shown in FIG. 1, fixation of the outer tube 2 is accomplished by an outer tube anchor nut 401 and an outer tube anchor block 402, wherein as shown in FIG. 4, the anchor nut 401 is fastened to said end of the outer tube 2, and the outer tube anchor block 402 has an outer thread that can engage an inner thread of the anchor nut 401. Of course, it is also possible for the outer tube 2 to be fixed to the outer tube anchor 40 by an adhesive. In addition, as shown in FIG. 4, the end of the outer tube 2 has an expanded configuration which enables this portion of the outer tube 2 to be firmly anchored between the outer tube anchor nut 401 and the outer tube anchor block 402. Further, the outer tube anchor block 402 is adjoined to a lateral end of the driving nut 205. This allows the outer tube 2 connect to the driving nut 205 via the outer tube anchor block 402, so that the outer tube 2, move axially in synchronization with the driving nut 205.

The inner tube anchor 50 is fixed to an inner tube section 3a of the inner tube 3 by a screw fit which allows adjustments in positional relations among the electric handle 1, the outer tube 2 and the inner tube 3 during their assembly. The inner tube anchor 50 is fixed to the lower section 302 of the handle.

Figure 5A:
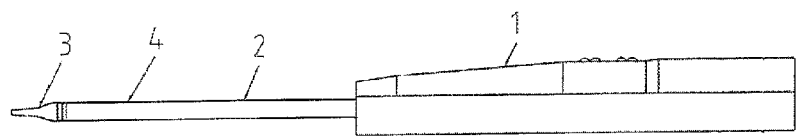
FIGS. 5a to 5b show a schematic overview of a delivery system in accordance with an embodiment of the present invention.

FIG. 5 shows a schematic overview of a delivery system in accordance with an embodiment of the present invention. As illustrated in FIG. 5a, this prosthetic valve delivery system includes the electric handle 1, the outer tube 2, the inner tube 3 and the prosthetic valve 4 (sheathed by the outer tube and not shown).

Figure 5B:
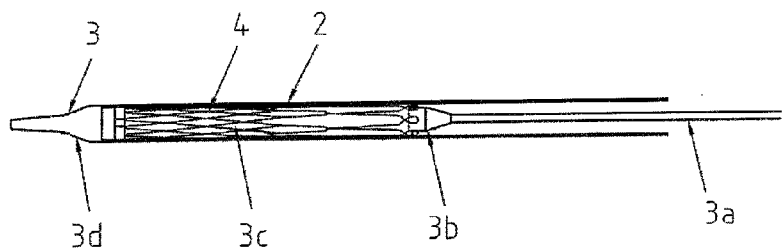

As shown in FIG. 5b, the inner tube 3 includes a guide cone 3d and a connector for the implant 3b. The prosthetic valve 4 is loaded on the inner tube 3 in a state of covering over an inner tube section 3c between the guide cone 3d and connector for the implant 3b and fixed to the connector for the implant 3b. A portion at one end of the inner tube section 3a proximal to the connector for the implant 3b is secured to the connector for the implant 3b, and its other end is attached to the lower section 302 of the handle by the inner tube anchor 50. This ensures the prosthetic valve 4 to remain fixed relative to the electric handle 1. In addition, the outer tube 2 shields over the inner tube 3 in order to cover the prosthetic valve 4 and is movable along the outer surface of the inner tube 3 activated by the motor 201. The inner tube section 3a of the inner tube 3 and an outer tube section of the outer tube 2, which are both proximal to the connector for the implant 3b, are both at least partially assembled into the electric handle 1, as shown in FIG. 5a.

Figure 6A:
Figure 6B:
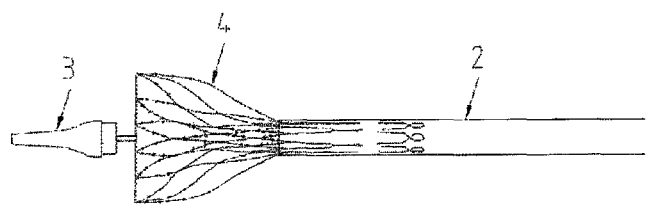
Figure 6C:
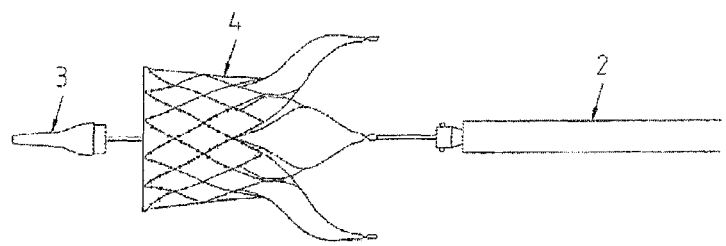

FIGS. 6a to 6c show a process of deploying the prosthetic valve 4 by the delivery system according to the present invention.

FIG. 6a shows the prosthetic valve 4 in a state before the deployment. As shown in FIG. 6b, those in the control buttons 102 enabling slow deployment (e.g., the advancement button and first gear button) are selected and manipulated to make the outer tube 2 retract slowly, thereby slowly deploying the prosthetic valve 4 from the delivery system. Upon correct deployment location having been confirmed, buttons for rapid deployment (e.g., the advancement button and second or multi-speed gear button) are selected to rapidly complete the deployment of the prosthetic valve 4, as shown in FIG. 6c. If it is needed to retrieve the prosthetic valve 4 for relocation during the positioning (i.e., the state as shown in FIG. 6b), a button enabling the retrieving (i.e., the retraction button) may be selected and manipulated to retrieve the prosthetic valve 4 completely within the delivery system (i.e., the state as shown in FIG. 6a), followed by another cycle of positioning and deployment operations.

Although the embodiments disclosed herein are described with reference to the case of delivering a prosthetic valve (e.g., a heart valve), it will be appreciated by those skilled in the art that the delivery system consistent with the present disclosure is also usable for the delivery of implants other than the prosthetic valve (e.g., a blood vessel stent) to a desired site in the human body.

The forgoing description of the embodiments disclosed herein enables those skilled in the art to implement or use the present invention. Various modifications of these embodiments are obvious to those of ordinary skill in the art. The general principles as defined herein are applicable to other embodiments without departing from the spirit or scope of the present invention. Thus, the present invention is not limited to the disclosed embodiments, but rather it covers all those within the broadest scope consistent with the principles as defined herein.

What is claimed is:

1. An electric handle for delivering an implant, comprising an electric control unit, a power-driven transmission mechanism, a handle housing, an outer tube anchor and an inner tube anchor, wherein: the electric control unit is operatively coupled to the power-driven transmission mechanism to actuate the power-driven transmission mechanism; the power-driven transmission mechanism is supported within the handle housing and moveable together with the outer tube anchor; the inner tube anchor is disposed within the handle housing and is configured to hold an inner tube of a delivery system; and the outer tube anchor is disposed within the handle housing to hold an outer tube of the delivery system, wherein the electric control unit comprises a controller, control buttons, a power switch, a power supply socket, and a power supply connector, the control buttons providing an instruction indicative of a direction and a speed, the controller receiving the instruction from the control buttons and converting the instruction into a signal recognizable by the power-driven transmission mechanism so as to actuate the power-driven transmission mechanism, the power switch connected to the controller or the control buttons via a cable so as to activate or deactivate the controller, the power supply socket coupled to the power supply connector, the power supply connector connected to a power supply so as to supply power to the electric control unit and the power-driven transmission mechanism.

2. The electric handle as recited in claim 1, wherein the power supply is integrated in the electric handle.

3. The electric handle as recited in claim 2, wherein the power-driven transmission mechanism comprises a motor, a shaft coupler, a threaded rod, a driving nut and a bearing, the motor being connected to the power supply socket and receiving the signal from the controller, the motor having an output coupled to the threaded rod via the shaft coupler, the threaded rod supported within the handle housing by the bearing, the threaded rod having an outer thread engaged with an inner thread of the driving nut.

4. The electric handle as recited in claim 2, wherein the inner tube anchor is fastened to the inner tube by a screw fit and is fixed within the handle housing.

5. The electric handle as recited in claim 1, wherein the power-driven transmission mechanism comprises a motor, a shaft coupler, a threaded rod, a driving nut and a bearing, the motor being connected to the power supply socket and receiving the signal from the controller, the motor having an output coupled to the threaded rod via the shaft coupler, the threaded rod supported within the handle housing by the bearing, the threaded rod having an outer thread engaged with an inner thread of the driving nut.

6. The electric handle as recited in claim 5, wherein the controller is integrated with the control buttons or with the motor.

7. The electric handle as recited in claim 5, wherein the outer tube anchor comprises an anchor nut and an outer tube anchor block, wherein: the anchor nut is fixed to one end of the outer tube; the outer tube anchor block has an outer thread that engages an inner thread of the anchor nut; and the outer tube anchor block is coupled to a lateral end of the driving nut so as to move in synchronization with the driving nut.

8. The electric handle as recited in claim 1, wherein the inner tube anchor is fastened to the inner tube by a screw fit and is fixed within the handle housing.

9. The electric handle as recited in claim 1, wherein the inner tube anchor is fastened to the inner tube by a screw fit and is fixed within the handle housing.

10. The method of using of an electric handle as defined in claim 1 for delivering a prosthetic valve.

11. A delivery system, comprising an outer tube, an inner tube and an implant, the inner tube comprising an inner tube section, a guide cone and a connector for the implant, the implant loaded on the section of the inner tube where it is located between the guide cone and the connector for the implant and attached to the connector for the implant, the outer tube shielding over the inner tube in order to cover the implant and being movable along the outer surface of the inner tube, the delivery system further comprising an electric handle as defined in claim 1, wherein: the outer tube and inner tube each has a portion proximal to the connector for the implant that is at least partially assembled into the electric handle; the outer tube anchor is configured to hold the outer tube such that the outer tube moves together with the outer tube anchor; and an end of the inner tube opposite to the guide cone is fixed within the handle housing by the inner tube anchor.

12. The delivery system as recited in claim 11, wherein the implant comprises a prosthetic valve.

13. The delivery system as recited in claim 12, wherein the prosthetic valve comprises a prosthetic heart valve.

14. The delivery system as recited in claim 11, wherein the implant comprises a blood vessel stent.

* * * * *